(12) United States Patent
Ishikawa

(10) Patent No.: US 10,849,562 B2
(45) Date of Patent: Dec. 1, 2020

(54) NOISE REDUCTION PROCESSING CIRCUIT AND METHOD, AND BIOLOGICAL INFORMATION PROCESSING DEVICE AND METHOD

(71) Applicant: SONY CORPORATION, Tokyo (JP)

(72) Inventor: Takanori Ishikawa, Saitama (JP)

(73) Assignee: SONY CORPORATION, Tokyo (JP)

( * ) Notice: Subject to any disclaimer, the term of this patent is extended or adjusted under 35 U.S.C. 154(b) by 293 days.

(21) Appl. No.: 15/576,358

(22) PCT Filed: Apr. 15, 2016

(86) PCT No.: PCT/JP2016/062091
§ 371 (c)(1),
(2) Date: Nov. 22, 2017

(87) PCT Pub. No.: WO2016/194490
PCT Pub. Date: Dec. 8, 2016

(65) Prior Publication Data
US 2018/0146926 A1   May 31, 2018

(30) Foreign Application Priority Data

Jun. 2, 2015   (JP) ................................. 2015-112215

(51) Int. Cl.
*A61B 5/00*   (2006.01)
*A61B 5/02*   (2006.01)
(Continued)

(52) U.S. Cl.
CPC ................ *A61B 5/721* (2013.01); *A61B 5/02* (2013.01); *A61B 5/0245* (2013.01);
(Continued)

(58) Field of Classification Search
CPC ...... A61B 5/721; A61B 5/7207; A61B 5/7203
See application file for complete search history.

(56) References Cited

U.S. PATENT DOCUMENTS

| 5,810,734 A * | 9/1998 | Caro ...................... A61B 5/022 600/301 |
| 2007/0056582 A1 * | 3/2007 | Wood ................... A61B 5/0059 128/200.24 |

(Continued)

FOREIGN PATENT DOCUMENTS

| JP | 11-276448 A | 10/1999 |
| JP | 2009-011585 A | 1/2009 |

(Continued)

OTHER PUBLICATIONS

International Search Report and Written Opinion of PCT Application No. PCT/JP2016/062091, dated Jul. 19, 2016, 09 pages of ISRWO.

*Primary Examiner* — Michael J Dalbo
(74) *Attorney, Agent, or Firm* — Chip Law Group

(57) ABSTRACT

A noise reduction processing circuit of the disclosure includes an adaptive filter that receives, as an input signal, a body motion signal that is filtered on a basis of a transfer function, that is calculated by modeling an influence of body motion on a blood flow, and a subtractor that outputs an error signal obtained by subtracting an output value of the adaptive filter from an observed signal.

11 Claims, 12 Drawing Sheets

(51) Int. Cl.
*A61B 5/0245* (2006.01)
*A61B 5/024* (2006.01)

(52) U.S. Cl.
CPC .......... *A61B 5/02416* (2013.01); *A61B 5/725* (2013.01); *A61B 2562/0219* (2013.01)

(56) References Cited

U.S. PATENT DOCUMENTS

| | | |
|---|---|---|
| 2009/0018408 A1 | 1/2009 | Ouchi et al. |
| 2010/0145171 A1* | 6/2010 | Park .................. A61B 5/1455 600/324 |
| 2010/0198087 A1* | 8/2010 | Takahashi .......... A61B 5/02438 600/500 |
| 2011/0025493 A1* | 2/2011 | Papadopoulos .... G08B 21/0446 340/539.12 |
| 2011/0098582 A1 | 4/2011 | Takahashi et al. |
| 2012/0059267 A1* | 3/2012 | Lamego ................ A61B 5/021 600/483 |
| 2014/0073936 A1* | 3/2014 | Rodriguez-Llorente .................... A61B 5/02416 600/476 |
| 2016/0120477 A1 | 5/2016 | Takahashi |

FOREIGN PATENT DOCUMENTS

| | | |
|---|---|---|
| JP | 2009-165590 A | 7/2009 |
| JP | 2009-195590 A | 9/2009 |
| JP | 2010-172645 A | 8/2010 |
| JP | 2011-092236 A | 5/2011 |
| JP | 2012-161507 A | 8/2012 |
| JP | 2013-202077 A | 10/2013 |
| JP | 2015-016188 A | 1/2015 |
| WO | 2015/004915 A1 | 1/2015 |

* cited by examiner

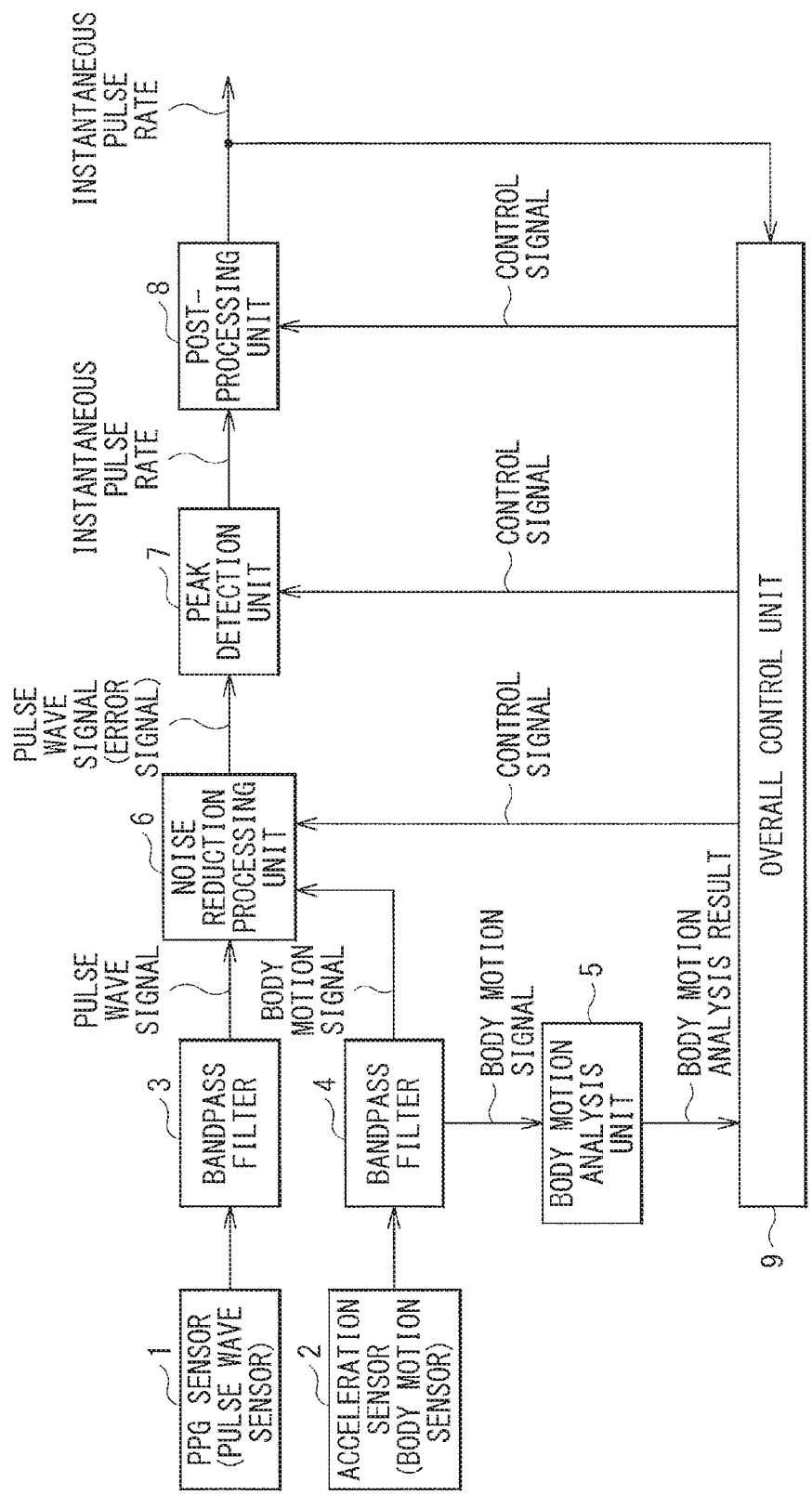
[FIG. 1]

[ FIG. 2 ]
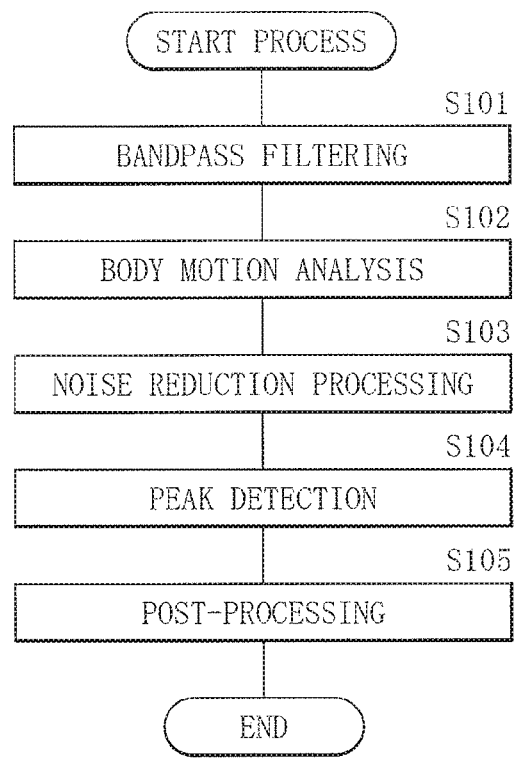

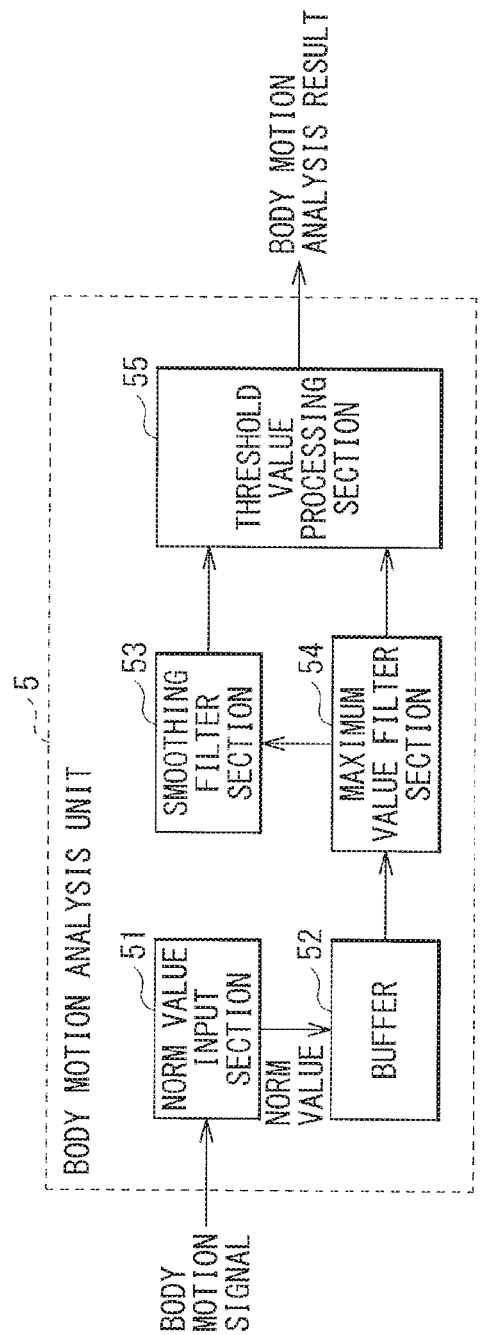

[ FIG. 4 ]
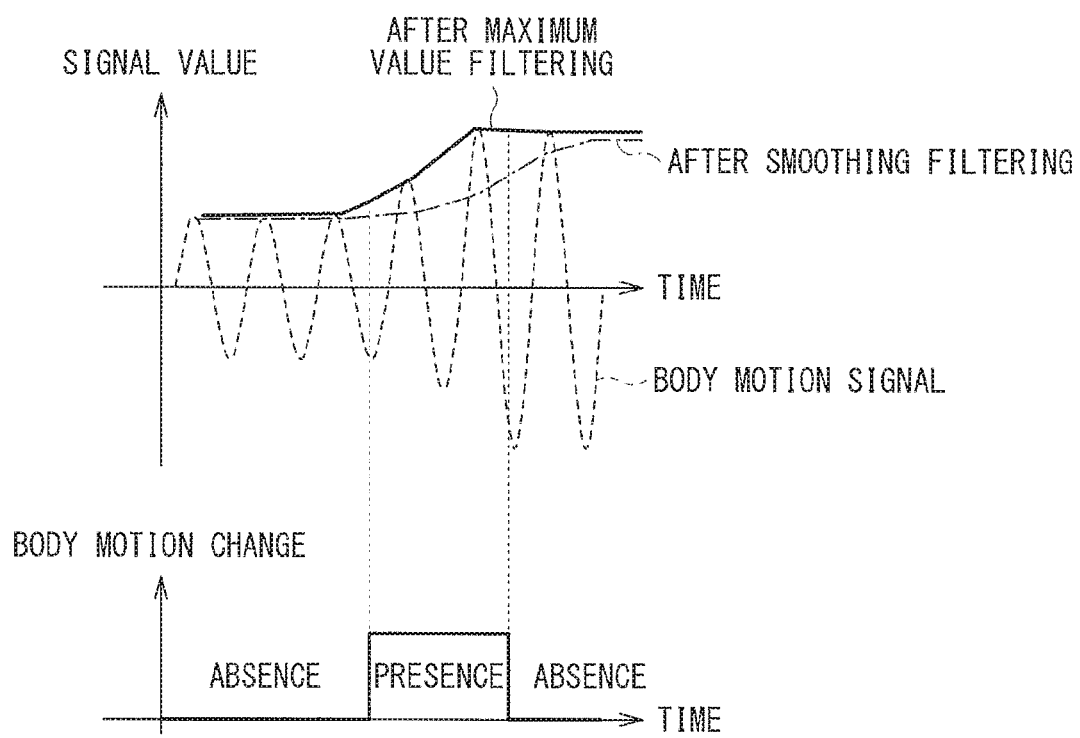

[ FIG. 5 ]
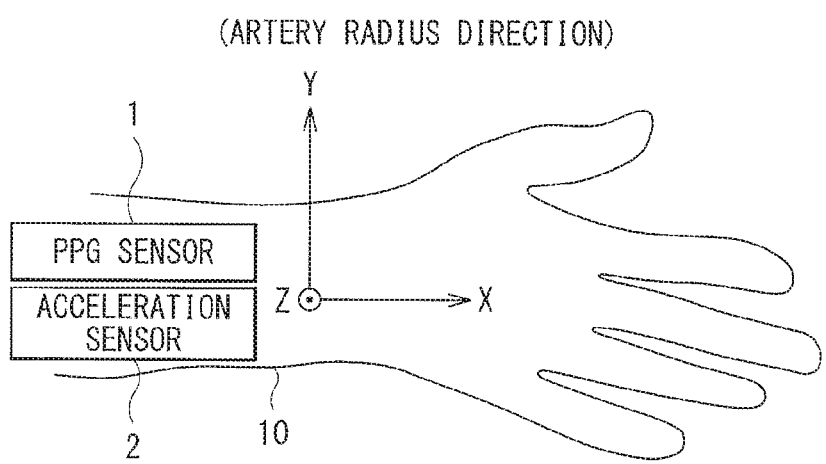
[ FIG. 6 ]
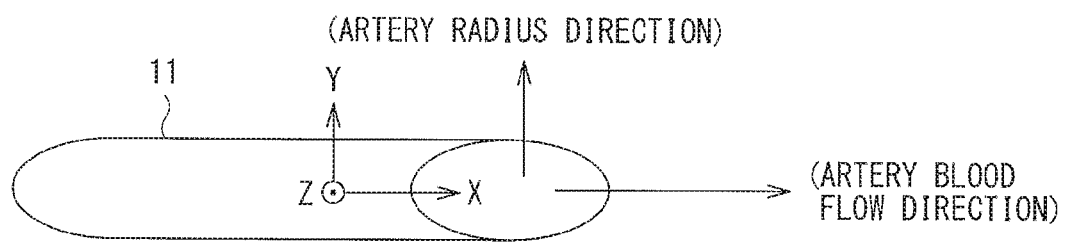

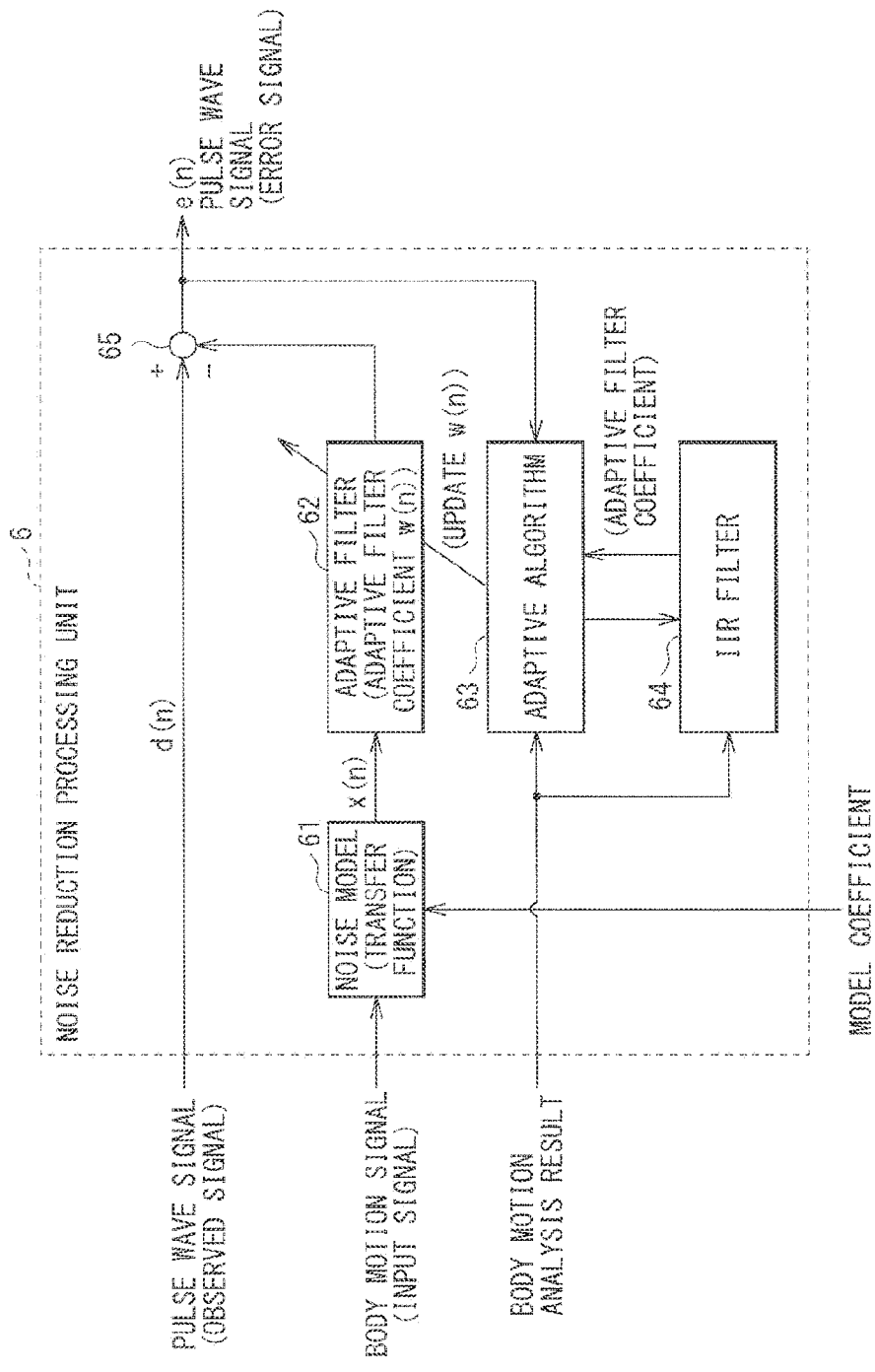

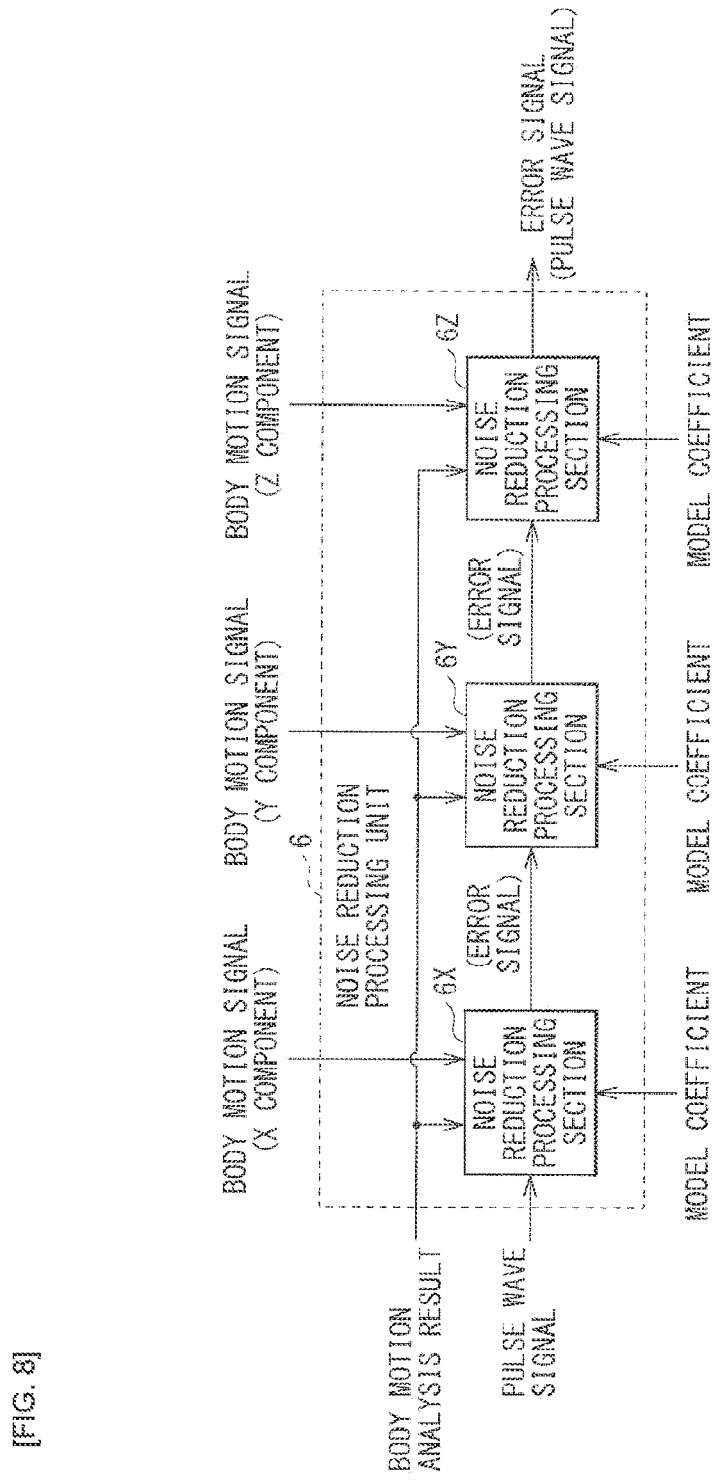
[FIG. 8]

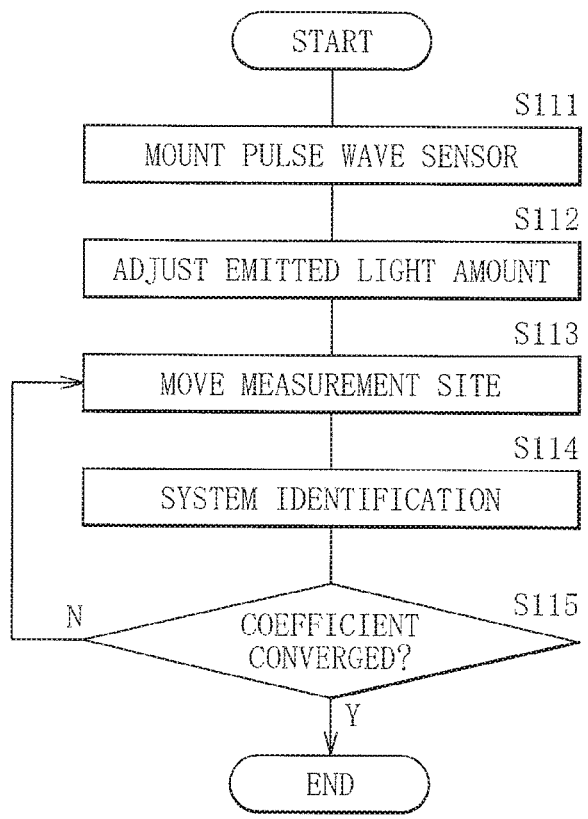
[ FIG. 9 ]

[ FIG. 10 ]
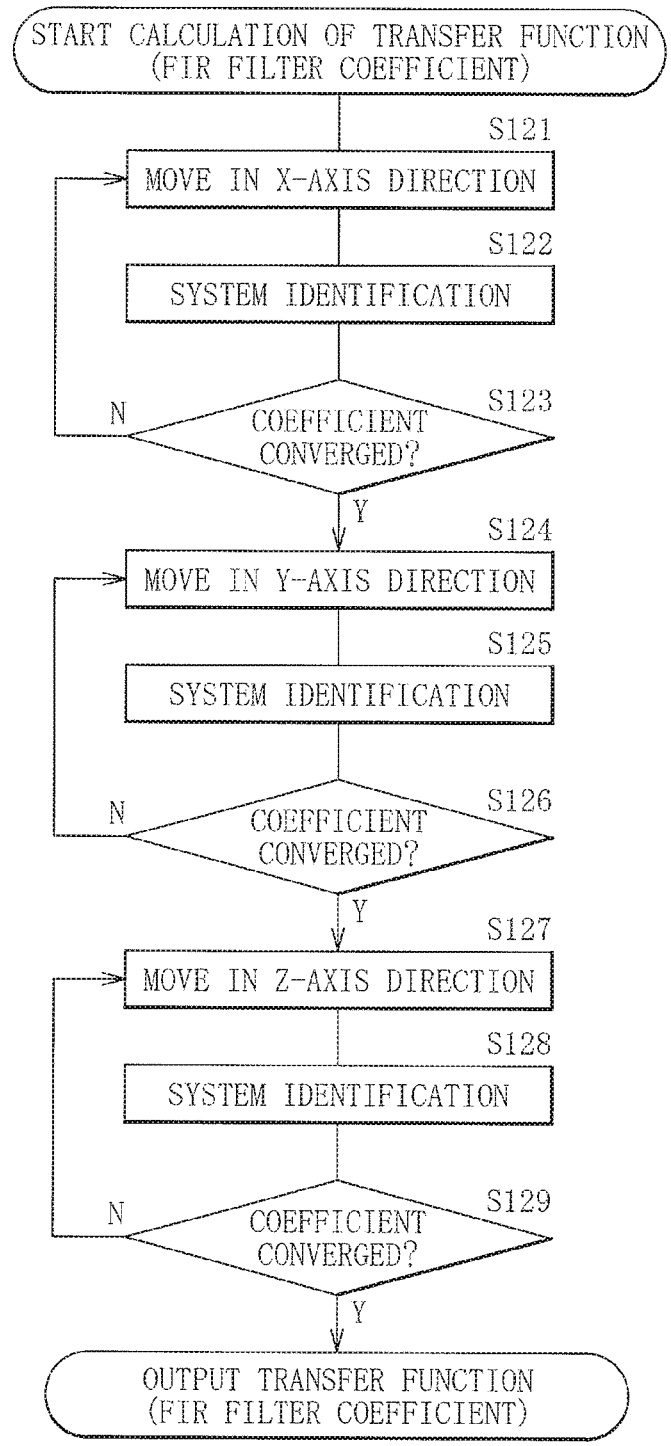

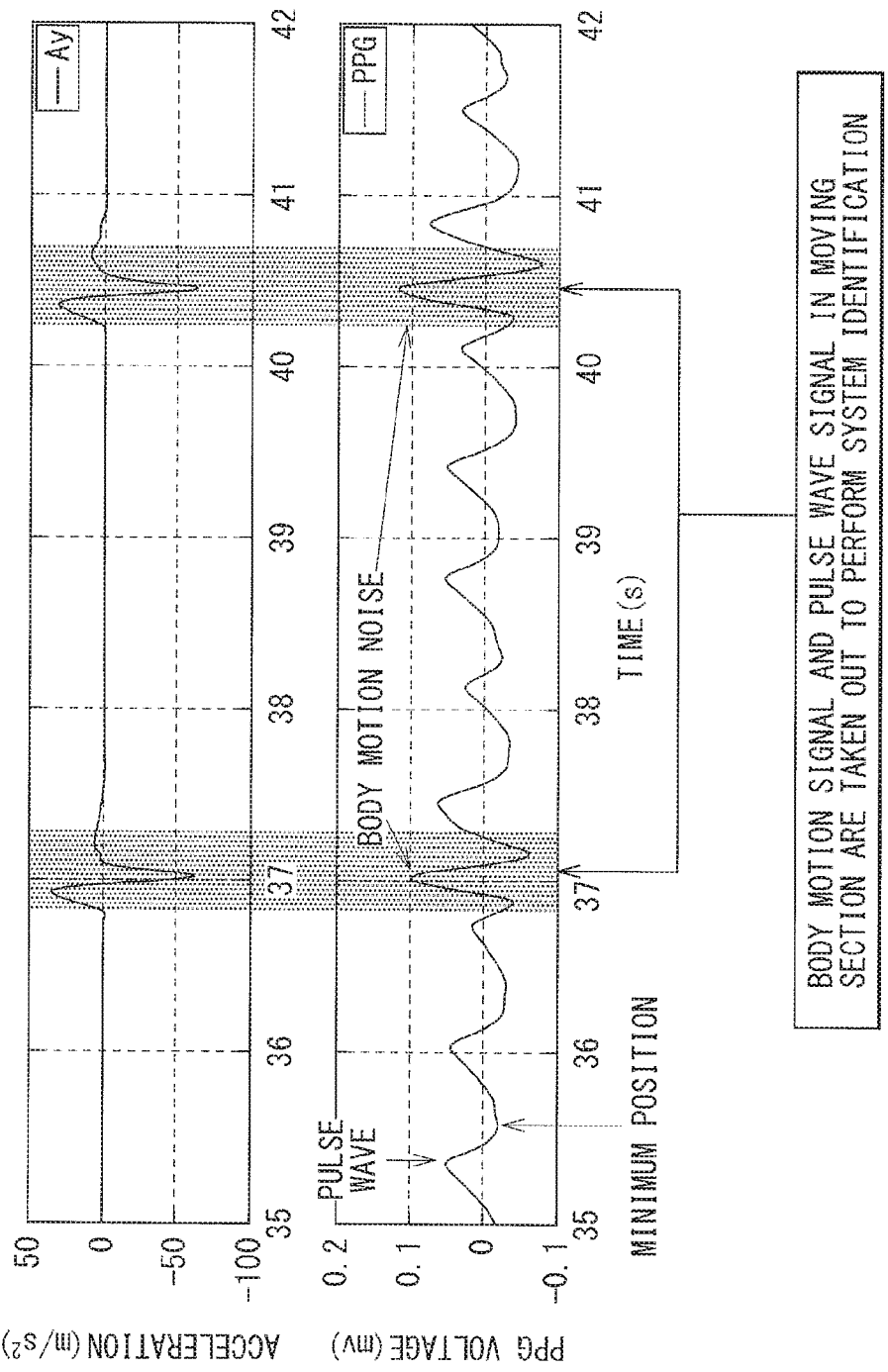
[FIG. 11]

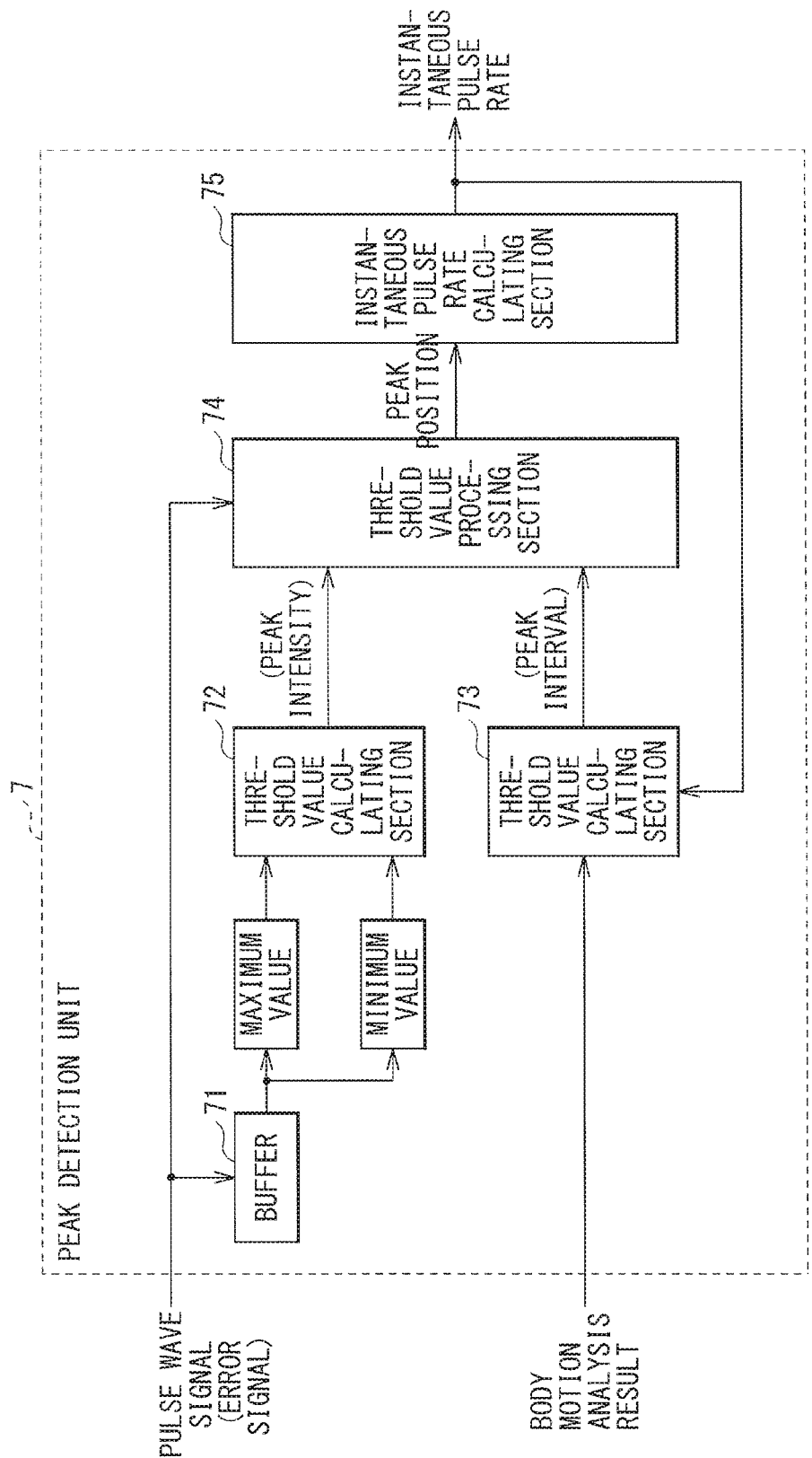
[ FIG. 12 ]

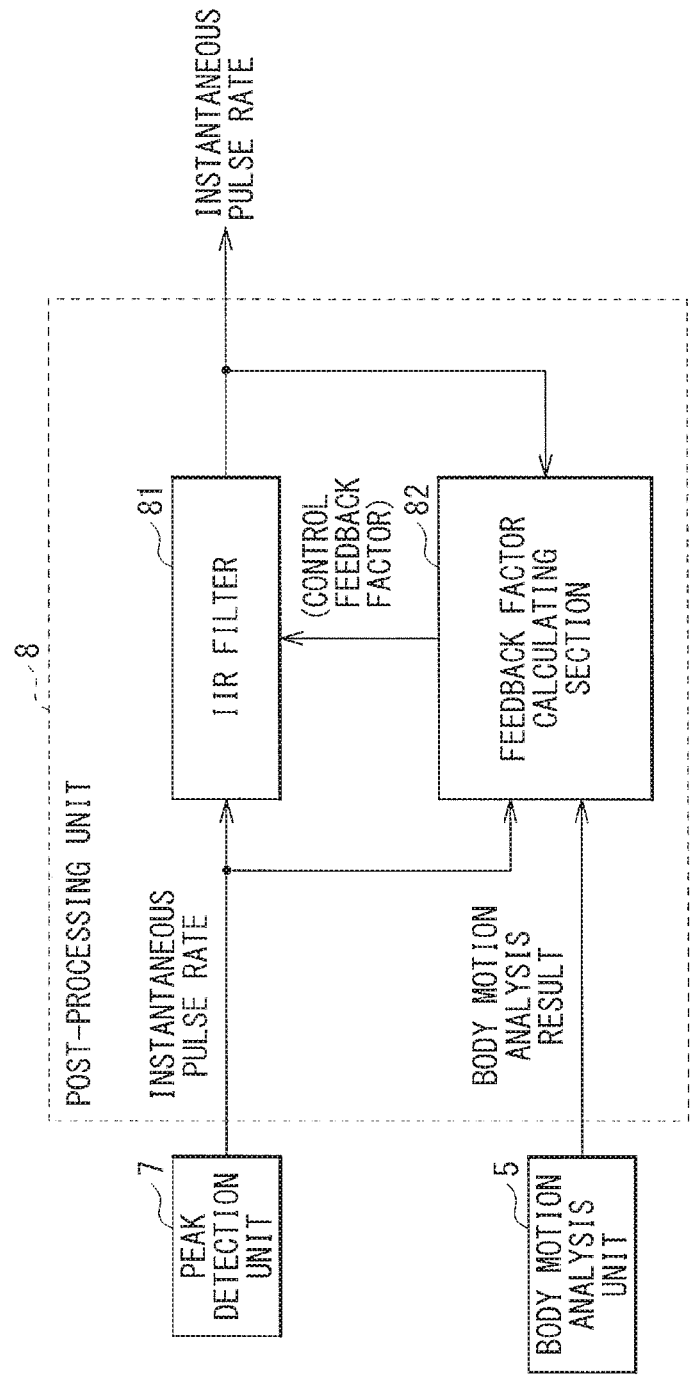
[ FIG. 13 ]

NOISE REDUCTION PROCESSING CIRCUIT AND METHOD, AND BIOLOGICAL INFORMATION PROCESSING DEVICE AND METHOD

CROSS REFERENCE TO RELATED APPLICATIONS

This application is a U.S. National Phase of International Patent Application No. PCT/JP2016/062091 filed on Apr. 15, 2016, which claims priority benefit of Japanese Patent Application No. JP 2015-112215 filed in the Japan Patent Office on Jun. 2, 2015. Each of the above-referenced applications is hereby incorporated herein by reference in its entirety.

TECHNICAL FIELD

The disclosure relates to noise reduction processing circuit and method for reducing a noise generated by body motion of a living body, and to biological information processing device and method.

BACKGROUND ART

Watch-type and wristband type devices each equipped with a heartbeat sensor oriented toward a heartbeat training have appeared on the market, with the recent boom of a health care and wellness; many of these devices adopt a photoelectric plethysmogram wave system (photoplethysmography, hereinafter, called a "PPG system").

CITATION LIST

Patent Literature

PTL 1: Japanese Unexamined Patent Application Publication No. H11-276448
PTL 2: Japanese Unexamined Patent Application Publication No. 2010-172645
PTL 3: Japanese Unexamined Patent Application Publication No. 2009-195590

SUMMARY OF THE INVENTION

In the PPG system, a pulse wave is measured in accordance with a fluctuation in volume of a blood flow. In the PPG system, a light ray is irradiated from a light emitting unit such as, for example, a Light Emitting Diode (LED) toward the skin. The irradiated light ray is absorbed into, scattered in, or reflected by the blood and a subcutaneous tissue that are present at a depth of about several millimeters (mm) under the skin. On this occasion, a change in blood flow in blood capillaries that are distributed under the skin is measured by measuring an amount of light that returns from under the skin by a light receiving unit such as, for example, a photodetector. In the following, a signal that is measured in this way is called a "pulse wave signal". In calculation of a pulse rate from the obtained pulse wave signal, for example, a maximum value position or a minimum value position of the pulse wave signal is detected, thereby making it possible to calculate a pulse rate that is instantaneous (hereinafter, called an "instantaneous pulse rate") from an inverse number of a time interval between the values. In general, the instantaneous pulse rate per minute is called the pulse rate or simply the pulse; it is said that the "pulse rate" and a "heart rate" are almost the same as each other unless there is any irregular pulse, pulse deficit, and so forth.

Although, the PPG system allows for comparatively accurate measurement of the pulse wave signal in a resting state, a noise (hereinafter, called a "body motion noise") caused by body motion is generated in an observed signal when a measurement site moves. Causes for the body motion noise are roughly divided into, for example, mixing of unnecessary skin surface reflection and mixing of natural light through under the skin caused by a change in contact state between a PPG sensor and the measurement site, and generation of a false signal caused by a blood flow change due to movement of the measurement site. Due to a combined cause of the above-mentioned main causes, a false peak signal is mixed into the pulse wave signal, thus making it difficult to discriminate which peak is a peak signal derived from pulsation, resulting in a possibility that an erroneous pulse rate may be calculated in a case where the instantaneous pulse rate is calculated from a time difference between peak positions.

As a technique for reducing the above-mentioned body motion noise, an adaptive filter has been proposed (for example, see PTL 1). The adaptive filter is a technique for automatically calculating an adaptive filter coefficient (w) that minimizes power of an error signal (e) when an observed signal (d) and an input signal (x) are given. In a case where the pulse wave signal is set as the observed signal, it is possible to separate the noise mixed into the observed signal by referring to a signal that has a high correlation with the noise as the input signal. Although various techniques has been proposed for computational algorithms, an arithmetic operation cost and a processing speed are in a trade-off relationship; the computational algorithms are selected depending on objects. In general, the least mean square (LMS) algorithm and the normalization least mean square (NLMS) algorithm are adopted.

In addition, as a technique for calculating the pulse rate, a frequency analysis method has been proposed (for example, see PTL 1). For example, the pulse wave signal that has been subjected to noise reduction processing is subjected to frequency analysis to determine, as the number of pulse waves, a frequency at which spectrum intensity reaches a maximum. This makes it possible to stably estimate the pulse rate during steady-state exercises, for example, when walking and running.

However, in the above-described noise reduction processing, when a body motion frequency is unsteady, for example, as in a case of standing up from a seated state and in a case of changing a running form, noise reduction performance is lowered. This is because a calculation time is necessary until an optimum value is obtained by following an abrupt change in the body motion frequency, due to difference in optimum adaptive filter coefficients for respective body motion patterns. Accordingly, there have been proposed a technique of replacing the previous one with an adaptive filter coefficient set in advance in a case where the body motion is abruptly changed (for example, see PTL 2), and a technique of setting the adaptive filter coefficient depending on types of the exercise (for example, see PTL 3). However, the body motion pattern and changes in the body motion frequency are different for respective users, and thus it is difficult to prepare the best coefficient in advance.

In addition, in a case of calculating the instantaneous pulse rate, it is difficult to accurately calculate, using the frequency analysis method, a fluctuation in the pulse, for example, when controlling one's breathing during running as well as a fluctuation in the pulse in a relaxed state when constantly measuring the pulse in an everyday life.

From the above, it is desired to establish a body motion noise reduction processing method which allows for prevention of a false detection even in a case where the body motion frequency constantly changes as in a case of measuring the instantaneous pulse rate in an everyday life.

It is desirable to provide noise reduction processing circuit and method, and biological information processing device and method that make it possible to accurately reduce a body motion noise included in the observed signal.

A noise reduction processing circuit according to an embodiment of the disclosure includes an adaptive filter that receives, as an input signal, a body motion signal that is filtered on a basis of a transfer function, that is calculated by modeling an influence of body motion on a blood flow, and a subtractor that outputs an error signal obtained by subtracting an output value of the adaptive filter from an observed signal.

A noise reduction processing method according to an embodiment of the disclosure includes inputting, as an input signal into an adaptive filter, the body motion signal filtered on a basis of a transfer function, that is calculated by modeling an influence of body motion on a blood flow, and subtracting an output value of the adaptive filter from an observed signal.

A biological information processing device according to an embodiment of the disclosure includes a pulse wave sensor that outputs a pulse wave signal, a body motion sensor that outputs a body motion signal, and a noise reduction processing unit that separates a body motion noise from the pulse wave signal. The noise reduction processing unit includes an adaptive filter that receives, as an input signal, the body motion signal that is filtered on a basis of a transfer function, that is calculated by modeling an influence of body motion on a blood flow, and a subtractor that inputs the pulse wave signal as an observed signal, and outputs an error signal obtained by subtracting an output value of the adaptive filter from the observed signal.

A biological information processing method according to an embodiment of the disclosure includes outputting a pulse wave signal from a pulse wave sensor, outputting a body motion signal from a body motion sensor, and performing noise reduction processing of separating a body motion noise from the pulse wave signal. The noise reduction processing includes inputting, as an input signal into an adaptive filter, the body motion signal that is filtered on a basis of a transfer function, that is calculated by modeling an influence of body motion on a blood flow, and inputting the pulse wave signal as an observed signal and outputting an error signal obtained by subtracting an output value of the adaptive filter from the observed signal.

In the noise reduction processing circuit or method, or in the biological information processing device or method according to an embodiment of the disclosure, a body motion signal that is filtered on a basis of a transfer function, that is calculated by modeling an influence of body motion on a blood flow, is inputted, as an input signal into an adaptive filter.

According to the noise reduction processing circuit or method, or the biological information processing device or method according to an embodiment of the disclosure, the body motion signal that is filtered on the basis of the transfer function, that is calculated by modeling the influence of the body motion on the blood flow, is inputted, as the input signal into the adaptive filter, thus making it possible to accurately reduce the body motion noise included in the observed signal.

It is to be noted that effects described here are not necessarily limitative, and may be any of the effects described herein.

BRIEF DESCRIPTION OF THE DRAWINGS

FIG. 1 is a block diagram illustrating a configuration example of a biological information processing device according to an embodiment of the disclosure.

FIG. 2 is a flowchart illustrating an overall operation of the biological information processing device.

FIG. 3 is a block diagram illustrating a configuration example of a body motion analysis unit.

FIG. 4 is an explanatory diagram schematically illustrating a conception of body motion analysis.

FIG. 5 is an explanatory diagram illustrating an example of a definition of axes in a measurement site.

FIG. 6 is an explanatory diagram illustrating an example of a definition of axes in an artery.

FIG. 7 is a block diagram illustrating a configuration example of a noise reduction processing unit.

FIG. 8 is a block diagram illustrating another configuration example of the noise reduction processing unit.

FIG. 9 is a flowchart illustrating an example of a process of determining a transfer function of body motion to a blood flow.

FIG. 10 is a flowchart illustrating an example of the process of determining the transfer function of body motion to the blood flow.

FIG. 11 is an explanatory diagram illustrating an example of each of a body motion signal and a pulse wave signal.

FIG. 12 is a block diagram illustrating a configuration example of a peak detection unit.

FIG. 13 is a block diagram illustrating a configuration example of a post-processing unit.

MODES FOR CARRYING OUT THE INVENTION

In the following, some embodiments of the disclosure are described in detail with reference to the drawings. It is to be noted that description is given in the following order.

1. Overall Description of Biological Information Processing Device (FIG. 1 and FIG. 2)
2. Description of Body Motion Analysis Unit (FIG. 3 to FIG. 6)
3. Description of Noise Reduction Processing Unit (FIG. 7 to FIG. 11)
4. Description of Peak Detection Unit (FIG. 12)
5. Description of Post-Processing Unit (FIG. 13)
6. Effects
7. Other Embodiments In the present embodiment, description is given of an example in which a technique of the disclosure is applied to a case of calculating an instantaneous pulse rate from a pulse wave signal in the PPG system. The technique of the disclosure includes the following contents (A) to (D).

(A) A noise reduction processing method that makes it possible to improve a convergence time and to follow a change in a body motion frequency by measuring body motion of a measurement site of a PPG sensor using an acceleration sensor and controlling an arithmetic operation parameter and a filter coefficient in calculation of an adaptive filter coefficient on the basis of a result of analysis of a body motion signal.

(B) In noise reduction processing, for example, body motion analysis results and transfer functions (FIR filter coefficients) of the body motion to the blood flow are calculated and recorded in one-to-one correspondence in advance instead of utilizing the body motion signal as it is as a reference signal (an input signal) of an adaptive filter; an appropriate filter coefficient is read out in accordance with the body motion signal, and a result of FIR filtering is inputted into the adaptive filter to thereby improve the convergence time.

(C) A peak detection method (an instantaneous pulse rate calculation method) of reducing a false detection of a false peak, as a peak derived from pulsation, that has not sufficiently been removed by means of body motion noise reduction processing or in a case where the intensity of the pulse wave signal is lowered, by adaptively setting threshold values (upper and lower limits of peak intensity and a peak interval) used for detecting the position of the peak derived from the pulsation from the obtained pulse wave signal.

(D) A post-processing filter that corrects a false detection (a false detection of the pulse rate caused by a body motion noise that has not been removed) that would occur even after the above-described noise reduction processing and peak detection processing are performed.

1. Overall Description of Biological Information Processing Device

FIG. 1 illustrates a configuration example of a biological information processing device according to an embodiment of the disclosure.

The biological information processing device includes a PPG sensor (a pulse wave sensor) 1, an acceleration sensor (a body motion sensor) 2, a bandpass filter 3, a bandpass filter 4, a body motion analysis unit 5, a noise reduction processing unit 6, a peak detection unit 7, a post-processing unit 8, and an overall control unit 9 that controls each of these components. The overall control unit 9 outputs a control signal to the noise reduction processing unit 6, the peak detection unit 7, and the post-processing unit 8.

The PPG sensor 1 includes, for example, a light emitting section such as an LED that irradiates light toward a measurement site such as, for example, a wrist and an arm, and a light receiving section such as a photodetector that detects an amount of light that has returned from under the skin of the measurement site.

FIG. 2 illustrates an example of an overall operation of the biological information processing device.

First, the bandpass filters 3 and 4 perform bandpass filtering (step S101). The bandpass filter 3 outputs a pulse wave signal that has been subjected to bandpass filtering in order to extract a fluctuation component associated with pulsation from an output signal of the PPG sensor 1. The bandpass filter 4 outputs a body motion signal that has been subjected to bandpass filtering in order to remove offset and electric noises caused by gravitational acceleration by the acceleration sensor 2.

Next, the body motion analysis unit 5 performs body motion analysis (step S102). On this occasion, the body motion analysis unit 5 analyses the body motion signal, and detects a body motion change of the measurement site.

Next, the noise reduction processing unit 6 performs noise reduction processing (step S103). On this occasion, the noise reduction processing unit 6 inputs the body motion signal as the input signal, and outputs, as the pulse wave signal, an error signal from which a false signal (the body motion noise) has been separated on the basis of an adaptive algorithm 63 described later (FIG. 7) that has the pulse wave signal being set as the observed signal. The false signal is included in the pulse wave signal, and is generated in association with the body motion Next, the peak detection unit 7 performs peak detection of the pulse wave signal (step S104). On this occasion, the peak detection unit 7 detects a peak position of the pulse wave signal that is generated in association with the pulsation on the basis of the pulse wave signal and the body motion analysis results, and outputs an instantaneous pulse rate.

Finally, the post-processing unit 8 performs post-processing (step S105). On this occasion, the post-processing unit 8 performs filtering based on the instantaneous pulse rate, the body motion analysis results, and the final instantaneous pulse rate (an output value of the post-processing unit 8) to thereby reduce a false detection of the instantaneous pulse rate caused by the body motion noise that has not been removed by the noise reduction processing unit 6 and the peak detection unit 7.

In the following, description is given in detail of each component of the biological information processing device using the drawings.

2. Description of Body Motion Analysis Unit

FIG. 3 illustrates a configuration example of the body motion analysis unit 5.

The body motion analysis unit 5 includes a norm value input section 51, a buffer 52, a maximum value filter section 53, a smoothing filter section 54, and a threshold value processing section 55.

The body motion analysis unit 5 detects the body motion change from the body motion signal. In a case where the acceleration sensor 2 is a three-axis acceleration sensor, a norm value of the body motion signal is inputted from the norm value input section 51 into the maximum value filter section 53 as the body motion signal. On this occasion, the maximum value filter section 53 may acquire only a signal value of a time interval that is considered to be necessary via the buffer 52. The body motion signal that has been subjected to maximum value filtering by the maximum value filter section 53 is inputted into the smoothing filter section 54 and the threshold value processing section 55. A difference between the body motion that has been subjected to the maximum value filtering by the maximum value filter section 53 and the body motion signal that has been smoothed and filtered by the smoothing filter section 54 is subjected to thresholding processing by the threshold value processing section 55 to detect a change in body motion observed when the body motion intensity and the body motion frequency of the measurement site are changed. In the present embodiment, as a smoothing filter in the smoothing filter section 54, for example, a finite impulse response (FIR) filter and an infinite impulse response (IIR) filter may be used.

FIG. 4 schematically illustrates a conception of body motion analysis by the body motion analysis unit 5. FIG. 4 illustrates, as the body motion analysis results, an example of analysis results of the body motion signal obtained during exercise. On the upper stage in FIG. 4, the vertical axis indicates a signal value, and the horizontal axis indicates time. On the lower stage in FIG. 4, the vertical axis indicates a state of the body motion change (presence or absence of the body motion change), and the horizontal axis indicates the time. The upper stage in FIG. 4 indicates the body motion signal obtained before filtering, the body motion signal obtained after smoothing and filtering, and the body motion signal obtained after maximum value filtering. It is possible to detect presence or absence of the body motion change, as illustrated on the lower stage in FIG. 4, from, for example, the body motion signal obtained after the smoothing and filtering and from the body motion signal obtained after the maximum value filtering, as illustrated on the upper stage in FIG. 4.

FIG. 5 and FIG. 6 illustrate respective examples of definitions of axes of a measurement site and an artery when performing the body motion analysis.

The PPG sensor 1 and the acceleration sensor 2 are incorporated into a portion of watch-type and wristband-type devices, and are mounted on the measurement site such as an arm 10 of the user, for example, as illustrated in FIG. 5. On this occasion, for example, as illustrated in FIG. 6, a direction of the blood flow in an artery 11 is set as an X-axis, and a radius direction of the artery 11 is set as a Y-axis on the measurement site. In addition, for example, a direction that is orthogonal to the blood flow direction of the artery 11 and the radius direction of the artery 11 is set as a Z-axis.

3. Description of Noise Reduction Processing Unit

FIG. 7 illustrates a configuration example of the noise reduction processing unit 6.

The noise reduction processing unit 6 includes an adaptive filter 62, an IIR filter 64, and a subtractor 65.

Suppose that an input signal (x) into the adaptive filter 62 is the body motion signal and that an observed signal (d) is the pulse wave signal. The noise reduction processing unit 6 outputs, as the pulse wave signal, an error signal (e) obtained by subtracting an output value of the adaptive filter 62 from the observed signal (d) using the subtractor 65.

In the present embodiment, description is given, by way of example, of a case where the adaptive algorithm 63 of the adaptive filter 62 is the NLMS algorithm. In the NLMS algorithm, an adaptive filter coefficient (w) of the adaptive filter 62 is updated by the following updating expression (2). It is to be noted that the present embodiment involves use of an FIR filter coefficient, as the adaptive filter coefficient (w), that has been calculated in advance in consideration of the influence of the body motion on the blood flow as described later. Suppose that n is a sample number. It follows that w (n+1) is an updated adaptive filter coefficient.

$$e(n) = d - w(n) \cdot x^T(n) \quad (1)$$

$$w(n+1) = w(n) + \mu \frac{e(n) \cdot x(n)}{\sum_{i=0}^{N-1} x^2(n-i)} \quad (2)$$

Here, (μ) is a positive constant that determines an update amount of the adaptive filter coefficient (w), and is called a step size. In the case of the present embodiment, the convergence time is improved by making the step size larger than usual in a preset time after detecting abrupt change in the body motion on the basis of the body motion analysis results. For example, the step size is multiplied by M only in a certain period of time. Although, in the present embodiment, the NLMS algorithm has been described by way of example, any other adaptive algorithm is adaptable similarly.

It is to be noted that, in the present embodiment, the adaptive algorithm 63 and the IIR filter 64 each correspond to a specific example of a coefficient updating section according to the technique of the disclosure.

In the adaptive filter 62, it is preferable that a correlation between the input signal (x) and the body motion noise be high in order to separate the body motion noise included in the observed signal (d). Instead of using the body motion signal as the input signal (x) as it is, the influence of the body motion on the blood flow is modeled as a noise model 61 and the transfer function (the FIR filter coefficient) of the body motion to the blood flow is calculated and recorded in advance. The body motion signal and a model coefficient are inputted into the noise model 61. The adaptive filter 62 utilizes results of FIR filtering on the body motion signal as the input signal (x) to allow the convergence time to be improved. In the convergence time, an optimum coefficient is obtained when the body motion intensity and the body motion frequency are changed.

FIG. 8 illustrates a configuration example of a case where the acceleration sensor 2 is the three-axis acceleration, as another configuration example of the noise reduction processing unit 6. It is sufficient that transfer functions of respective components of the three-axis acceleration to the blood flow be calculated in advance to form a configuration in which noise reduction processing sections 6X, 6Y, and 6Z for respective acceleration components X, Y, and Z are cascaded.

For example, the model coefficient, the X component of the body motion signal, the body motion analysis results, and the pulse wave signal obtained before the noise reduction processing are inputted into the noise reduction processing section 6X. The model coefficient, the Y component of the body motion signal, the body motion analysis results, and an output (an error signal) from the noise reduction processing section 6X are inputted into the noise reduction processing section 6Y. The model coefficient, the Z component of the body motion signal, the body motion analysis results, and an output (an error signal) from the noise reduction processing section 6Y are inputted into the noise reduction processing section 6Z. An output (an error signal) from the noise reduction processing section 6Z is set as the pulse wave signal.

Incidentally, the transfer function depends on states of a blood vessel, the blood flow therein, and so forth, and thus there is an optimum coefficient for each user or individual. Accordingly, in the biological information processing device according to the present embodiment, the transfer function of the body motion to the blood flow is determined in advance as the noise model 61 before determining the instantaneous pulse rate. FIG. 9 illustrates an example of a process of determining the noise model 61 (a process of determining the transfer function of the body motion to the blood flow).

First, for example, as illustrated in FIG. 5, the PPG sensor 1 as the pulse wave sensor is mounted on the measurement site such as the arm 10 by the user (step S111). An amount of return light varies among individual users depending on the color of the skin of the measurement site. Therefore, the biological information processing device controls a light amount of the light emitting section of the pulse wave sensor to allow the pulse wave signal to be less saturated in a resting state. (step S112).

Next, the biological information processing device urges the user to move the measurement site (step S113). This causes the biological information device to exert impulsive body motion in an artery blood flow direction (see FIG. 6), thus measuring the pulse wave signal and the body motion signal. Next, in the biological information processing device, the noise reduction processing unit 6 performs system identification using the adaptive filter 62, with the body motion signal being inputted as the input signal and the pulse wave signal being outputted as the output signal (step S114).

Next, the biological information processing device determines whether the transfer function (the FIR filter coefficient) has converged (step S115). In a case where it is determined that the transfer function has not converged (step S115: N), the flow returns to the process in step S113. In a case where it is determined that the transfer function has converged (step S115: Y), the flow ends the process.

FIG. 10 illustrates an example of a process of determining the transfer function of the body motion to the blood flow.

First, the biological information processing device urges the user to move the measurement site in an X-axis direction (step S121), and the noise reduction processing unit 6 performs system identification using the adaptive filter 62, with the body motion signal being inputted as the input signal and the pulse wave signal being outputted as the output signal (step S122). Next, the biological information device determines whether a transfer function (an FIR filter function) regarding the X-axis direction has converged (step S123). In a case where the biological information processing device determines that the transfer function regarding the X-axis direction has not converged (step S123: N), the flow returns to the process in step S121.

In a case where it is determined that the transfer function regarding the X-axis direction has converged (step S123: Y), the biological information processing device then urges the user to move the measurement site in an Y-axis direction (step S124), and the noise reduction processing unit 6 performs the system identification using the adaptive filter 62, with the body motion signal being inputted as the input signal and the pulse wave signal being outputted as the output signal (step S125). Next, the biological information processing device determines whether a transfer function (an FIR filter function) regarding the Y-axis direction has converged (step S126). In a case where the biological information processing device determines that the transfer function regarding the Y-axis direction has not converged (step S126: N), the flow returns to the process in step S124.

In a case where it is determined that the transfer function regarding the Y-axis direction has converged (step S126: Y), the biological information processing device urges the user to move the measurement site in a Z-axis direction (step S127), and the noise reduction processing unit 6 performs the system identification using the adaptive filter 62, with the body motion signal being inputted as the input signal and the pulse wave signal being outputted as the output signal (step S128). Next, the biological information processing device determines whether a transfer function (an FIR filter function) regarding the Z-axis direction has converged (step S129). In a case where the biological information processing device determines that the transfer function regarding the Z-axis direction has not converged (step S129: N), the flow returns to the process in step S127. In a case where the biological information processing device determines that the transfer function regarding the Z-axis direction has converged (step S129: Y), the flow ends the process.

FIG. 11 illustrates an example of each of the body motion signal outputted from the acceleration sensor 2 and the pulse wave signal outputted from the PPG sensor 1. In FIG. 11, the upper stage illustrates an example of the body motion signal, and the lower stage illustrates an example of the pulse wave signal. In FIG. 11, the horizontal axis indicates time, the upper-stage vertical axis indicates acceleration, and the lower-stage vertical axis indicates an output value (a PPG voltage) of the PPG sensor 1.

The biological information processing device urges the user to move the measurement site, for example, at the initial use stage of the device in order to determine the above-mentioned transfer functions in advance. The biological information processing device detects, for example, a minimum value of the pulse wave, and notifies the user of the position thereof with sound, and so forth. For example, the user moves the arm 10 in a designated direction while hearing the sound in synchronized timing. The biological information processing device takes out the body motion signal and the pulse wave signal in a section across which the measurement site is moving, and performs the system identification through the processes in FIG. 9 and FIG. 10.

It is to be noted that, although the description has been given hereinabove of the transfer function (the FIR filter coefficient) of the body motion to the blood flow by way of example of the noise model 61, approximation by a polynomial of degree N may be also conceived as another embodiment. A coefficient of the polynomial of degree N may be calculated by using, for example, the least squares method, and so forth.

In addition, in the noise reduction processing unit 6, the determined adaptive filter coefficient is subjected to IIR filtering using the IIR filter 64. In a case where it is determined that the user is in a resting state, for example, with the past value one sample before being set to 0 (zero) value, adaptive filtering is set OFF by setting the IIR filtering ON. During exercise, the adaptive filtering is set ON by setting a feedback factor to 0.0 and setting the IIR filtering OFF. This configuration allows for smooth switching between presence and absence of the adaptive filtering by simply controlling the feedback factor of the IIR filter 64 in accordance with the body motion analysis results.

The above-mentioned ideas allows for improvement in the convergence time of the adaptive filtering, the noise reduction effect is sufficiently obtained, irrespective of abrupt changes in body motion intensity and the body motion frequency.

4. Description of Peak Detection Unit

FIG. 12 illustrates a configuration example of the peak detection unit 7.

The peak detection unit 7 includes a buffer 71, a threshold value calculating section 72, a threshold value calculating section 73, a threshold value processing section 74, and an instantaneous pulse rate calculating section 75.

There are cases where a contact state of the PPG sensor 1 is changed by the body motion to cause the pulse wave signal intensity to be modulated. When peak detection is performed using a preset fixed threshold value in this case, there may be cases where detection of the position of the peak derived from pulsation is not possible. In addition, there is also a possibility that a false peak caused by the body motion noise may be detected in error as the peak derived from pulsation; for example, an abnormal value that is not more than 50 (pulse rate/sec.) and is not less than 200 (pulse rate/sec.) is detected as the instantaneous pulse rate of a general adult during exercise.

In the present embodiment, a threshold value th of the peak intensity is determined from a maximum value vmax and a minimum value vmin of the pulse wave signal in a certain analysis window, as represented by the following expressions (3) and (4), in the threshold value calculating section 72 to prevent generation of such a detection error as mentioned above. The maximum value vmax and the minimum value vmin of the pulse wave signal are inputted into the threshold value calculating section 72 via the buffer 71.

$$th = v\min + \alpha \cdot (v\max - v\min) \tag{3}$$

$$0 < \alpha < 1 \tag{4}$$

This allows the threshold value th of the peak intensity to be adaptively controlled in accordance with the intensity of the pulse wave signal, thus making it possible to detect the peak positon, irrespective of the modulation of the pulse wave signal intensity.

In addition, in the present embodiment, threshold value calculating section 73 determines threshold values (upper and lower limits) of a peak interval IBI (Inter Beat Interval) from the body motion analysis results and the past instantaneous pulse rate in order to reduce a false detection of the false peak caused by the body motion. For example, the threshold values are determined as represented by the following expressions (5) and (6).

$$IBI_{upper} = \left(\frac{1}{N}\sum_{i=1}^{N} IBI_{t-i}\right) + \beta \tag{5}$$

$$IBI_{lower} = \left(\frac{1}{N}\sum_{i=1}^{N} IBI_{t-i}\right) - \beta \tag{6}$$

Here, β is a threshold value used for determining a bandwidth of the peak interval IBI. β either may be a preset fixed value, or may be set large in the resting state and set small during exercise on the basis of the body motion analysis results.

The threshold value processing section 74 performs adaptive thresholding on the pulse wave signal for peak detection. The instantaneous pulse rate calculating section 75 calculates the instantaneous pulse rate from an inverse of a time difference between the peak positions obtained by the threshold value processing section 74. This allows for reduction of the false detection of the false peak caused by the body motion noise that has not been completely removed by the noise reduction processing unit 6, thus making it possible to improve the accuracy of the instantaneous pulse rate.

5. Description of Post-Processing Unit

FIG. 13 illustrates a configuration example of the post-processing unit 8.

The post-processing unit 8 includes an IIR filter 81 and a feedback factor calculating section 82. The post-processing unit 8 causes the feedback factor calculating section 82 to control the feedback factor of the IIR filter 81.

There are cases where the above-described noise reduction processing unit 6 and peak detection unit 7 do not completely remove the noise, thus causing an abnormal value to occur in a time change of the instantaneous pulse rate. In general, time correlation of the instantaneous pulse rate is very high. Accordingly, in a case where the time change of the instantaneous pulse rate is larger than a preset threshold value, the feedback factor calculating section 82 controls the feedback factor of the IIR filter 81 to increase (to a value close to, for example, 1.0), thus making it possible to extrapolate the past instantaneous pulse rate as it is and to modify (reduce) a false detection. In addition, the feedback factor calculating section 82 controls the feedback factor of the IIR filter 81 to have a value smaller than 1.0, for example, about 0.5 during exercise, thus making it possible to stabilize the instantaneous pulse rate.

6. Effects

According to the present embodiment, the body motion signal that has been filtered on the basis of the transfer function calculated by modeling the influence of the body motion on the blood flow is inputted, as the input signal, into the adaptive filter 62 of the noise reduction processing unit 6, thus making it possible to accurately reduce the body motion noise included in the observed signal.

According to the present embodiment, in noise reduction processing by the adaptive filter 62 of the noise reduction processing unit 6, the convergence time of the adaptive filtering is improved by performing update control of the step size of the adaptive filter 62, modeling of the body motion to the blood flow, and the adaptive filter coefficient on the basis of the body motion signal by the acceleration sensor 2. This makes it possible to sufficiently obtain the noise reduction effect even in a case where the body motion intensity and the body motion frequency are abruptly changed.

In addition, according to the present embodiment, the adaptive thresholding performed by the peak detection unit 7 on the basis of the pulse wave signal allows for detection of the peak position associated with pulsation, even when the contact state of the PPG sensor 1 is changed by the body motion to change the intensity of the pulse wave signal, and even when the false peak is present that is caused by a reduction in S/N and the body motion noise, thus making it possible to calculate a highly reliable instantaneous pulse rate.

In addition, according to the present embodiment, the feedback factor of the IIR filter 81 is controlled on the basis of the body motion signal analysis results in stabilization processing of the instantaneous pulse rate in the post-processing unit 8, thus making it possible to perform time stabilization processing of the instantaneous pulse rate with ease.

It is to be noted that the effects described herein are merely illustrative and are not necessarily limitative; the effects may further include other effects.

7. Other Embodiments

The technique according to the disclosure is not limited to the description of the foregoing embodiment, and may be modified in a variety of ways.

For example, the technology may have the following configurations.

(1)

A noise reduction processing circuit including:

an adaptive filter that receives, as an input signal, a body motion signal that is filtered on a basis of a transfer function, the transfer function being calculated by modeling an influence of body motion on a blood flow; and a subtractor that outputs an error signal obtained by subtracting an output value of the adaptive filter from an observed signal.

(2)

The noise reduction processing circuit according to (1), in which the observed signal includes a pulse wave signal outputted from a pulse wave sensor, and the transfer function is determined by system identification from the body motion signal and the observed signal obtained when impulsive body motion is exerted to a pulse wave measurement site sensed by the pulse wave sensor.

(3)

The noise reduction processing circuit according to (1) or (2), further including a coefficient updating section that updates an adaptive filter coefficient of the adaptive filter on a basis of a result of body motion analysis, the body motion analysis indicating a body motion change that is detected by analyzing the body motion signal.

(4)

The noise reduction processing circuit according to (3), in which the coefficient updating section includes an IIR filter that performs IIR filtering on the adaptive filter coefficient in accordance with the result of the body motion analysis.

(5)

A noise reduction processing method including:

inputting, as an input signal into an adaptive filter, the body motion signal filtered on a basis of a transfer function, the transfer function being calculated by modeling an influence of body motion on a blood flow; and subtracting an output value of the adaptive filter from an observed signal.

(6)

A biological information processing device including:

a pulse wave sensor that outputs a pulse wave signal;

a body motion sensor that outputs a body motion signal; and a noise reduction processing unit that separates a body motion noise from the pulse wave signal, the noise reduction processing unit including an adaptive filter that receives, as an input signal, the body motion signal that is filtered on a basis of a transfer function, the transfer function being calculated by modeling an influence of body motion on a blood flow, and a subtractor that inputs the pulse wave signal as an observed signal, and outputs an error signal obtained by subtracting an output value of the adaptive filter from the observed signal.

(7)

The biological information processing device according to (6), further including:

a peak detection unit that detects a peak position of the pulse wave signal in association with pulsation on a basis of the error signal, and calculates an instantaneous pulse rate; and a post-processing unit that performs processing of reducing a false detection of the instantaneous pulse rate caused by the body motion noise.

(8)

The biological information processing device according to (7), in which the peak detection unit detects the peak position by performing adaptive thresholding on the error signal.

(9)

The biological information processing device according to (8), in which the peak detection unit calculates a threshold value of peak intensity when detecting the peak position in accordance with intensity of the error signal.

(10)

The biological information processing device according to (8) or (9), further including a body motion analysis unit that detects a body motion change by analyzing the body motion signal, and outputs a detection result as a result of body motion analysis, in which the peak detection unit calculates a threshold value of a peak interval to be used when detecting the peak position from the result of the body motion analysis and the previously calculated instantaneous pulse rate.

(11)

The biological information processing device according to any one of (7) to (10), further including a body motion analysis unit that detects a body motion change by analyzing the body motion signal, and outputs a detection result as a result of body motion analysist, in which the post-processing unit includes an IIR filter that performs IIR filtering on the instantaneous pulse rate, and a feedback factor calculating section that controls a feedback factor of the IIR filter on a basis of the result of the body motion analysis.

(12)

A biological information processing method including:

outputting a pulse wave signal from a pulse wave sensor;

outputting a body motion signal from a body motion sensor; and performing noise reduction processing of separating a body motion noise from the pulse wave signal, the noise reduction processing including inputting, as an input signal into an adaptive filter, the body motion signal that is filtered on a basis of a transfer function, the transfer function being calculated by modeling an influence of body motion on a blood flow, and inputting the pulse wave signal as an observed signal and outputting an error signal obtained by subtracting an output value of the adaptive filter from the observed signal.

The present application is based on and claims priority from Japanese Patent Application No. 2015-112215 filed with the Japan Patent Office on Jun. 2, 2015, the entire contents of which is hereby incorporated by reference.

It should be understood by those skilled in the art that various modifications, combinations, sub-combinations and alterations may occur depending on design requirements and other factors insofar as they are within the scope of the appended claims or the equivalents thereof.

The invention claimed is:

1. An apparatus, comprising:

a noise reduction processing unit configured to separate a body motion noise from a pulse wave signal acquired from a pulse wave sensor, wherein the noise reduction processing unit includes:

an adaptive filter configured to:

receive, as an input signal, a body motion signal from a body motion sensor; and filter the input signal based on a transfer function that indicates an influence of body motion on a blood flow; and a subtractor configured to:

input the pulse wave signal as an observed signal;

obtain an error signal based on subtraction of an output value of the adaptive filter from the observed signal; and output the error signal;

a peak detector configured to:

detect a peak position of the observed signal based on the error signal; and calculate an instantaneous pulse rate based on the detected peak position of the observed signal; and a post-processing unit configured to reduce a false detection of the instantaneous pulse rate, wherein the false detection is based on the body motion noise.

2. The apparatus according to claim 1, wherein the transfer function is determined based on an impulsive body motion on a pulse wave measurement site sensed by the pulse wave sensor.

3. The apparatus according to claim 1, further comprising a coefficient updating section configured to:
 detect a body motion change based on analysis of the body motion signal;
 determine a detection result based on the detected body motion change; and
 update an adaptive filter coefficient of the adaptive filter based on the detection result.

4. The apparatus according to claim 3, wherein
 the coefficient updating section includes an infinite impulse response (IIR) filter, and
 the IIR filter is configured to execute an IIR filtering process on the adaptive filter coefficient based on the detection result.

5. A method, comprising:
 separating, by a noise reduction processing unit of an apparatus, a body motion noise from a pulse wave signal, wherein
 the pulse wave signal is acquired from a pulse wave sensor, and
 the separating includes:
  receiving, by an adaptive filter of the noise reduction processing unit, a body motion signal from a body motion sensor as an input signal;
  filtering, by the adaptive filter, the input signal based on a transfer function that indicates an influence of body motion on a blood flow;
  inputting, by a subtractor of the noise reduction processing unit, the pulse wave signal as an observed signal;
  subtracting, by the subtractor, an output value of the adaptive filter from the observed signal;
  obtaining, by the subtractor, an error signal based on the subtraction; and
  outputting, by the subtractor, the error signal;
 detecting, by a peak detector of the apparatus, a peak position of the observed signal based on the error signal;
 calculating, by the peak detector, an instantaneous pulse rate based on the detected peak position of the observed signal; and
 reducing, by a post-processing unit of the apparatus, a false detection of the instantaneous pulse rate, wherein the false detection is based on the body motion noise.

6. A biological information processing device, comprising:
 a pulse wave sensor configured to output a pulse wave signal;
 a body motion sensor configured to output a body motion signal;
 a noise reduction processing unit configured to separate a body motion noise from the pulse wave signal, wherein the noise reduction processing unit includes:
  an adaptive filter configured to:
   receive, as an input signal, the body motion signal; and
   filter the input signal based on a transfer function that indicates an influence of body motion on a blood flow; and
  a subtractor configured to:
   input the pulse wave signal as an observed signal;
   obtain an error signal based on subtraction of an output value of the adaptive filter from the observed signal; and
   output the error signal;
 a peak detection unit configured to:
  detect a peak position of the observed signal based on the error signal; and
  calculate an instantaneous pulse rate based on the detected peak position of the observed signal; and
 a post-processing unit configured to reduce a false detection of the instantaneous pulse rate, wherein the false detection is based on the body motion noise.

7. The biological information processing device according to claim 6, wherein the peak detection unit is further configured to:
 execute an adaptive thresholding process on the error signal; and
 detect the peak position based on the adaptive thresholding process on the error signal.

8. The biological information processing device according to claim 7, wherein the peak detection unit is further configured to:
 calculate a threshold value of peak intensity based on the adaptive thresholding process; and
 detect the peak position based on intensity of the error signal and the threshold value of peak intensity.

9. The biological information processing device according to claim 7, further comprising a body motion analysis unit configured to:
 detect a body motion change based on analysis of the body motion signal;
 generate a detection result based on the detected body motion change; and
 output the detection result,
 wherein the peak detection unit is further configured to:
  calculate a threshold value of a peak interval based on the detection result; and
  detect the peak position based on the detected body motion change, the threshold value of the peak interval, and the instantaneous pulse rate.

10. The biological information processing device according to claim 6, further comprising a body motion analysis unit configured to:
 detect a body motion change based on analysis of the body motion signal;
 generate a detection result based on the detected body motion change; and
 output the detection result, wherein the post-processing unit includes:
  an infinite impulse response (IIR) filter configured to execute an IIR filter process on the instantaneous pulse rate; and
  a feedback factor calculating section configured to control a feedback factor of the IIR filter based on the detection result.

11. A biological information processing method, comprising:
 in a biological information processing device:
 outputting, by a pulse wave sensor of the biological information processing device, a pulse wave signal;
 outputting, by a body motion sensor of the biological information processing device, a body motion signal;
 separating, by a noise reduction processing unit of the biological information processing device, a body motion noise from the pulse wave signal, wherein the separating includes:

receiving, by an adaptive filter of the noise reduction processing unit, the body motion signal as an input signal, filtering, by the adaptive filter, the input signal based on a transfer function that indicates an influence of body motion on a blood flow, inputting, by a subtractor of the noise reduction processing unit, the pulse wave signal as an observed signal, obtaining, by the subtractor, an error signal based on subtraction of an output value of the adaptive filter from the observed signal, and outputting, by the subtractor, the error signal;

detecting, by a peak detection unit of the biological information processing device, a peak position of the observed signal based on the error signal;

calculating, by the peak detection unit, an instantaneous pulse rate based on the detected peak position of the observed signal; and reducing, by a post-processing unit of the biological information processing device, a false detection of the instantaneous pulse rate, wherein the false detection is based on the body motion noise.

\* \* \* \* \*